United States Patent
Stevens et al.

(10) Patent No.: US 10,442,827 B2
(45) Date of Patent: *Oct. 15, 2019

(54) METHOD FOR PURIFICATION OF LECITHIN

(71) Applicant: Cargill, Incorporated, Wayzata, MN (US)

(72) Inventors: Robert Stevens, Riethoven (NE); Jos Van Denderen, Hulst (NE)

(73) Assignee: Cargill, Incorporated, Wayzata, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/833,299

(22) Filed: Dec. 6, 2017

(65) Prior Publication Data
US 2018/0094008 A1 Apr. 5, 2018

Related U.S. Application Data

(62) Division of application No. 15/033,180, filed as application No. PCT/US2014/063053 on Oct. 30, 2014, now Pat. No. 9,856,277.

(30) Foreign Application Priority Data
Oct. 30, 2013 (EP) .................................... 13190800

(51) Int. Cl.
C07F 9/10 (2006.01)
A23J 7/00 (2006.01)
A23L 33/00 (2016.01)
C11B 3/10 (2006.01)

(52) U.S. Cl.
CPC .............. C07F 9/103 (2013.01); A23J 7/00 (2013.01); A23L 33/40 (2016.08); C07F 9/10 (2013.01); A23V 2002/00 (2013.01); C11B 3/10 (2013.01)

(58) Field of Classification Search
CPC .............. A23J 7/00; C07F 9/10; C07F 9/103
See application file for complete search history.

(56) References Cited

U.S. PATENT DOCUMENTS

2017/0247647 A1* 8/2017 Lee .................... C12G 3/06

FOREIGN PATENT DOCUMENTS

| CN | 101016312 A | 8/2007 |
| CN | 102657273 A | 9/2012 |
| WO | 2009/095435 A1 | 8/2009 |
| WO | 2014/099726 A1 | 6/2014 |

OTHER PUBLICATIONS

Myre, E., et al., The turbidity tube: Simple and accurate measurement of turbidity in the field, 2006, Department of Civil and Environmental Engineering, Michigan Technology University, 17 pages (Year: 2006).*
Nieuwenhuyzen, W. V., et al., Update on vegetable lecithin and phospholipid technologies, 2008, Eur. J. Sci. Technol, vol. 110, pp. 472-486 (Year: 2008).*
Szuhaj, B. F., Lecithins: Sources, Manufacture & Uses, 1989, The American Oil Chemists' Society, Abstract of Chapter 3, Cherry et al., pp. 16 & 29: Chapter 10, Lantz, pp. 162-164 & Chapter 15, Zeisel, pp. 225-228, (12 pages) (Year: 1989).*
The Vitamin Shoppe, Liquid Lecithin, 2015, abstract, 3 pages (year 2015).*
Szuhaj, B. F., Lecithin, 2005, Baileys Industrial Oil and Fat Products, 13::13, pp. 1-98 (Year: 2005).*
Database WPI, Week 200808, Aug. 15, 2007, Thomson Scientific, London, GB; AN 2008-B17077, XP002719538 & CN 101016312 A (CUI P).
Database WPI, Week 201309, Sep. 12, 2012, Thomson Scientific, London, GB; AN 2012-R02157, XP002719539 & CN 102657273A (Beijing Lvyuanqiuzheng Technology Dev Co).

* cited by examiner

Primary Examiner — Yate' K Cutliff

(57) ABSTRACT

The present invention relates to a method for the purification of lecithin, comprising the steps of (a) mixing lecithin with active carbon to form a dispersion; then (b) mixing an organic solvent into the dispersion; then (c) separating the active carbon and contaminants from the lecithin preferably through gravitational forces. The invention further relates to a lecithin substantially free of contaminants, and a food or feed product comprising said lecithin.

17 Claims, No Drawings

METHOD FOR PURIFICATION OF LECITHIN

CROSS-REFERENCE TO RELATED APPLICATIONS

This application is a divisional of U.S. patent application Ser. No. 15/033,180, filed 29 Apr. 2016, entitled METHOD FOR THE PURIFICATION OF LECITHIN, which claims the benefit of PCT Patent Application, Serial No. PCT/US2014/063053, Filed 30 Oct. 2014, entitled METHOD FOR THE PURIFICATION OF LECITHIN, which claims the benefit of priority to European Application No. 13190800.6 filed 30 Oct. 2013, entitled METHOD FOR THE PURIFICATION OF LECITHIN, which are hereby incorporated by reference in their entirety.

FIELD OF THE INVENTION

The present invention relates to a method for the purification of lecithin or gums preferably of the vegetable origin. The invention further relates to purified lecithin, purified gums and food products comprising thereof.

BACKGROUND OF THE INVENTION

Lecithin may become contaminated with e.g. poly-aromatic hydrocarbons (PAHs), pesticides and other contaminants during its extraction process from oil seeds. Some of these contaminants, and especially PAHs, can be carcinogenic and pose a problem when the lecithin is to be used in food and animal feed, and especially in infant food products.

Methods for removing contaminants from lecithin are well known in the art. For example, CN 2007/1010356 discloses a method for preparing a powdered lecithin intended for medical use, containing only traces of solvent or coal. The method thereof makes use of supercritical $CO_2$ to extract contaminants from a raw lecithin sample followed by bleaching with active carbon to remove unwanted pigments.

Methods for removing PAHs from liquids have been described in the art. For example, U.S. Pat. No. 6,270,676 describes a process for removing ethers and/or polycyclic aromatic hydrocarbons from water. The process requires adsorbing the contaminants on an adsorber resin of divinyl benzene/styrene copolymer, then desorbing the adsorbed contaminants with steam and finally regenerating the adsorber resin. The methods of the prior art are however not directly applicable to lecithin. This is because lecithin is too viscous. As such, putting the lecithin through a packed column or a filter is very difficult.

A lecithin suitable for use in infant food formulas and having an increased degree of purity together with a method for manufacturing thereof are also known from WO 2009/095435. However, according to this publication the term "purified lecithin" means a lecithin having reduced amounts of triglyceride fractions, e.g. ω6 long chain polyunsaturated fatty acids (LCPUFA). WO 2009/095435 is not concerned with PAH that may be present in the lecithin, nor does it disclose any method that could remove or at least decrease the amount of the PAH.

It is thus an object of the present invention to provide a method for the purification of lecithin that may be capable of effectively and economically removing contaminants such as e.g. PAHs, pesticides, particulates, and the like. A further object of the invention may be to provide a lecithin having reduced amounts of contaminants, e.g. PAH.

SUMMARY OF THE INVENTION

In a first aspect, the present invention relates to a method for the purification of lecithin or gums, wherein said lecithin or gums are preferably of vegetable origin. The method comprises the steps of:
   a. mixing a lecithin or a gum with active carbon to form a dispersion; then
   b. mixing an organic solvent into the dispersion; then
   c. separating the active carbon and contaminants from the lecithin or from the gum, preferably through gravitational forces.

In a second aspect, the present invention relates to a lecithin or a gum which is substantially free of poly-aromatic hydrocarbons, and preferably also substantially free of pesticides, herbicides, insecticides, heavy metals, organic solvents and particulates.

In a third aspect, the present invention relates to a food or feed product comprising the purified lecithin or the purified gum. The food product is preferably an infant food product.

DETAILED DESCRIPTION

The present invention relates to a method for the purification of lecithin or of gums.

Lecithin includes a family of polar lipids, including phospholipids. Typically phospholipids are found in cell membrane structures and have a tendency to aggregate into structures, such as, for example, lamellar, hexagonal structures. A phospholipid or phosphatide is a molecule that is similar to a triglyceride, except that the sn3 position has a phosphate group and a functional group attached, rather than a third fatty acyl chain. Major phosphatides existing in plant oils include, for example, phosphatidyl choline (PC), phosphatidyl ethanolamine (PE), phospatidyl serine, phosphatidyl glycerol, phosphatidyl inositol (PI), and phosphatidyl acid (PA). Lecithin also contains non-phosphatide components including, for example, triglycerides, sterols, tocopherols, and carbohydrates.

Lecithin or gums may be a by-product of oil-production processes. Lecithin and gums are typically produced after oil extraction and before the oil-refining process. Because it is a by-product, the quality of the lecithin or of the gum may vary depending, in part, on the quality and type of seeds from which the oils are produced. Lecithin or gums may be produced from any vegetable oil, including, but not limited to, soybean oil, sunflower oil, corn oil, cottonseed oil, palm oil and rapeseed oil. Lecithin or gums also may be of animal origin, such as, for example, fish or eggs. Commercially available lecithins may be derived from soybeans, rapeseed, and sunflower seeds, and are available both in liquid form (e.g. dissolved in soybean or other edible oil) or in dry powdered form. Many lecithins are obtained from vegetable oil by mixing vegetable oil with water, which hydrates the lecithin and renders it substantially insoluble in the vegetable oil, thereby permitting centrifugal separation of the hydrated lecithin (known as gums) from the oil. The separated gums may be dried to provide a lecithin and redissolved in a suitable edible oil to provide a lecithin with a desired viscosity. Preferred lecithin as used in the process of the present invention, is lecithin in liquid form.

In some embodiments, the lecithin or the gum can be a modified lecithin or gum. Examples of a modified lecithin include, but are not limited to, hydrolyzed lecithin, acetylated lecithin and hydroxylated lecithin. Lecithin contains functional groups (e.g., double bonds) that make it reactive in a number of chemical reactions. As used herein the term "modified lecithin" refers to lecithin molecules that have been modified by reaction of one or more of the functional groups (e.g., double bonds) of the phosphatides with one or more reagents or enzymes that modify the chemical composition of the phosphatides.

In some embodiments, the lecithin is a PC rich lecithin. In some embodiments, the PC rich lecithin is PC enriched, which means the lecithin has undergone a fractionation process and is PC fractionated. A typical method to fractionate lecithin is by adding alcohol to the lecithin in order to separate the lecithin into a PC rich fraction and a PC poor fraction. A PC rich lecithin formed by this process would be an alcohol fractionated PC enriched lecithin. In some embodiments, the PC rich lecithin is a lecithin containing a certain amount of phosphatidyl choline (PC), but the lecithin is not fractionated. In some embodiments, a PC concentration of the PC rich lecithin is at least about 30 wt %. As described in further detail below, the PC concentration of lecithin is based on the acetone insoluble fraction of lecithin. It is recognized that PC rich lecithin may be formed by other known methods, such as, for example, adjusting pH.

Lecithin may be characterized by the amount of phosphatides in the lecithin, which may be determined by the "acetone insolubility (AI)" method defined in American Oil Chemists' Society (AOCS) Method Ja 4-46. As such, all types of lecithin may be expressed in terms of a percentage of acetone insolubles. For example, standard soy-based lecithin typically contains about 62 to 64 wt % AI; plastic soy lecithin typically contains a minimum of about 65 wt % to 69 wt % AI. A soy bean lecithin with an AI of 62% consists typically of 12-18% PC, 10-15% PE, 8-11% PI, 3-8% PA, 5-7% glycolipids, 2-3% sterols, 5% carbohydrates, 36% of triglycerides, and 1% of moisture. The AI fraction is the same as the polar fraction of the lecithin, and contains the phospholipids, glycolipids and sterols and carbohydrates.

In some embodiments, the percentage of acetone insolubles in the lecithin composition is between about 50 wt % and about 98 wt %. Typically, modified lecithin has an acetone insolubility of about 50 wt % or greater, for example, about 52 wt % or greater, about 54 wt % or greater, about 56 wt % or greater, about 58 wt % or greater, or about 60 wt % or greater. In some embodiments having PC rich lecithin, the PC concentration is at least about 30 wt % of the total amount of acetone insolubles; in other embodiments the PC concentration is at least about 40 wt % of the total amount of acetone insolubles; at least about 50 wt % of the total amount of acetone insolubles; at least about 60 wt % of the total amount of acetone insolubles; and at least about 70 wt % of the total amount of acetone insolubles. The invention also relates to gums having a percentage of acetone insoluble as defined immediately hereinabove.

Lecithin or gums may however still contain contaminants such as e.g. poly-aromatic hydrocarbons (PAHs), pesticides, herbicides, fungicides, insecticides, heavy metals and particulates which should be removed. The process according to the present invention allows for the removal of these contaminants.

The first step of the process of the present invention comprises mixing lecithin or gum with active carbon to form a dispersion. The active carbon can adsorb contaminants such as poly-aromatic hydrocarbons (PAHs), pesticides, herbicides, fungicides, insecticides, heavy metals. The active carbon should be mixed such that it is efficiently spread throughout the lecithin or throughout the gum for a sufficient period of time so that the contaminants can come in contact with the active carbon and be adsorbed thereto. The mixing conditions should be such that the active carbon is preferably uniformly dispersed throughout the lecithin or throughout the gum and that it remains in dispersion (not sedimenting). In one embodiment, in step (a) of the process of the present invention, the active carbon is mixed with the lecithin or with the gum for a period of from about 1 hour to about 120 hours, preferably from about 2 hours to about 100 hours, even more preferably from about 12 hours to about 72 hours, and most preferably from about 24 hours to about 48 hours. A uniform dispersion can be obtained by mixing for example with a paddle stirrer at e.g. 100 rpm.

In one embodiment, the active carbon is powdered active carbon. The powdered active carbon preferably has an average diameter of from about 1 μm to about 100 μm, more preferably from about 1 μm to about 25 μm. Preferably, the powdered active carbon contains particles having a volume average particle size of preferably between 1 μm and 50 μm, more preferably between 10 μm and 45 μm, most preferably between 20 μm and 40 μm. The volume average particle size refers to a particle size at 50% (average particle size D50) in a cumulative volume particle size distribution measured by a laser diffraction particle size analyzer. In another embodiment, the active carbon is granulated active carbon. Preferably, about 90 wt % of the granulated active carbon has an average diameter of from about 0.2 mm to about 4 mm, preferably from about 0.3 mm to about 3 mm, even more preferably from about 0.4 mm to about 2 mm. In yet another embodiment, the active carbon may be a combination of powdered and granulated active carbon. The average diameter of active carbon particles may be determined using the well-known SEM imagery technique by measuring the largest measurable distance between two points on the periphery of a particle. A number of at least 100 particles are preferably measured. To aid in the counting and diameter measurement of a large number of particles, an image analysis software may be used, e.g. Image-Pro Plus from Media Cybernetics.

The active carbon may be mixed with lecithin or with gum at a level of from about 0.01% to about 3%, preferably from about 0.05% to about 2%, even more preferably from about 1% to about 1.5%, by weight of the lecithin or gum, respectively.

In one embodiment, in step (a) of the process of the present invention, the lecithin or the gum is at a temperature of from about 10° C. to about 100° C., preferably from about 10° C. to about 90° C., more preferably from about 15° C. to about 80° C., even more preferably from about 30° C. to about 70° C., most preferably from about 40° C. to about 60° C.

In the second step (b) of the process, an organic solvent is mixed into the dispersion obtained from step (a). Preferred organic solvents are hexane, ethanol, heptane and toluene. The most preferred organic solvent is hexane. The organic solvent is preferably at a temperature of from about 1° C. above its melting temperature to about 1° C. below its boiling point, preferably at a temperature from about 10° C. to about 60° C., more preferably from about 10° C. to about 40° C., and even more preferably at about room temperature.

The organic solvent is mixed into the dispersion at a weight ratio of lecithin (or gum) to organic solvent of from about 6:1 to about 1:30, more preferably from about 3:1 to about 1:20, even more preferably from about 3:2 to about 1:10, most preferably from 1:1 to 1:4. In case the organic solvent is hexane, the weight ratio lecithin (or gum):hexane is preferably from 2:1 to 1:8, more preferably 1:1 to 1:6, most preferably from 1:2 to 1:4. In case the organic solvent is ethanol, the ratio lecithin (or gum):ethanol is preferably from 6:1 to 3:1, more preferably from 5:1 to 3:1, most preferably about 4:1.

In a third step of the process of the present invention, the active carbon (with contaminants adsorbed thereto) together with other contaminants, especially particulates which are not soluble in the organic solvent, are preferably separated from the lecithin or from the gum in a single step. The active carbon and contaminants are preferably removed from the lecithin or from the gum by means of gravitational forces. Suitable devices for separation include decanters (e.g. GEA Westfalia Model CA 225; Oelde, Germany) and disk stack centrifuges/separators (e.g. GEA Westfalia Model SC 6; Oelde, Germany).

In a preferred embodiment, the active carbon and other contaminants together with the lecithin or with the gum and the organic solvent are fed to the separation device with a feeding rate of at least 10% of a processing capacity of said device, more preferably with a feeding rate of at least 30% of said processing capacity, even more preferably with a feeding rate of at least 45% of said processing capacity, most preferably with a feeding rate of at least 60% of said processing capacity. It was surprisingly observed that improved results were obtained at increased feeding rates. Preferably, the feeding rate is between 20% and 80%, more preferably between 30% and 75%, most preferably between 65% and 70% of the processing capacity of the device.

The organic solvent is then preferably removed from the lecithin for example by evaporation, and lecithin is recovered. Optionally, the recovered lecithin may further be filtrated.

In a preferred embodiment, the method for lecithin or gum purification in accordance with the invention comprises the steps of:
 a) mixing lecithin or gum with active carbon to form a dispersion;
 b) subsequently, mixing an organic solvent, preferably hexane, into the dispersion; then
 c) separating the active carbon and contaminants from the lecithin or from the gum preferably through gravitational forces, thereby producing a residue containing the active carbon and contaminants and further producing a first stream containing lecithin or gum and the organic solvent; and
 d) removing the organic solvent from said first stream with a solvent-removal process containing a stripping step, preferably a steam-stripping step, thereby obtaining solvent-free lecithin or solvent-free gum and further obtaining a waste stream containing water and the organic solvent.

Said contaminants may include in addition to PAH also other residues insoluble in the said organic solvent.

In a preferred embodiment, said step d) also contains a solvent evaporation step, wherein a quantity of the organic solvent is evaporated from the first stream. Preferably, said evaporation step is a multi-stage evaporation step, i.e. the evaporation of the organic solvent from the first stream is carried out in at least two stages. Preferably, the evaporation step is carried out under vacuum. The stripping step can be carried out between the evaporation stages or before or after said evaporation stages.

The steam-stripping step is a well-known method to remove solvents from miscella wherein stripping steam is mainly used to dilute the vapor content of the organic solvent at the lecithin or gum surface to minimize recondensation of said organic solvent vapors back into the lecithin or into the gum. Usually stripping columns are used to carry out the steam-stripping step, such as columns with structured packing, random packing, bubble cap trays and disc and donut packing. Preferably, a lecithin (or gum): stripping steam weight ratio of between 1 and 50 is used, more preferably said ratio is between 1.5 and 30, even more preferably said ratio is between 2 and 10, most preferably between 2 and 5. Preferably, stripping is carried out under vacuum, preferably at a pressure of between 10 and 150 mbar, even more preferably between 25 and 100 mbar, most preferably between 50 and 75 mbar. During the steam stripping the organic solvent evaporates and its vapors are captured and condensed into a recovered solvent flux, which can be re-used. Another waste stream produced during steam-stripping is a stream containing water and organic solvent. In order to safely release said waste stream into the environment, it is preferred that the organic solvent is removed from the water to an extent sufficient to at least comply with environmental legislation. However, waste handling processes are usually energy expensive and may be rather difficult to implement as they usually comprise several waste handling steps and involve a rather long retention time. The present inventors however developed a new waste treatment method which may be easily added as an additional step to the method of purifying lecithin in accordance with the invention.

Preferably, the waste stream obtained at step d) hereinabove, containing water and the organic solvent is mixed in a subsequent step e) with steam to heat said waste stream up and to pressurize it; and subsequently flash-evaporating the organic solvent to obtain a waste water stream. Step e) may be repeated until the organic solvent concentration in the waste water stream is reduced to the desired level. Preferably, step e) is repeated at least once, more preferably at least twice. It was observed that the waste treatment step may allow an important reduction of the organic solvent concentration level in the waste water stream and at the same time, said step can be easily implemented into the method of purifying lecithin or gum of the present invention in an optimum way.

By flash-evaporating the organic solvent is herein understood a process wherein the pressurized waste stream undergoes a reduction in pressure, e.g. by passing through a throttling valve or other throttling device. The flash-evaporation usually occurs within a vessel, which is referred to in the art as flash drum. During said reduction in pressure within the flash drum, at least part, preferably all, of the waste stream transforms (or "flashes") into vapor and subsequently cooled to below a saturation temperature of the water but preferably above a saturation temperature of the organic solvent. A condensor attached to the flash drum may be used to collect the solvent's vapors and condense them into a solvent flux, which may be re-used.

Preferably, the waste stream is heated up by using steam to a temperature of at least 100° C., more preferably at least 120 ° C., most preferably at least 130° C. Preferably said temperature does not exceed 150° C.

Preferably, the waste stream is pressurized at step e) above 1 atm, more preferably to at least 2 atm, most preferably to at least 3 atm. The pressure in the flash drum is lower than the pressure of said stream and is preferably substantially equal with the atmospheric pressure.

The temperature in the flash drum at which said stream is allowed to expand (to "flash") is preferably at least 75° C., more preferably at least 85° C., most preferably at least 95° C. Preferably said temperature is below 100° C. In case step e) is repeated, the temperature in the second (and subsequent) flash drum is at least 95° C., more preferably about 100° C.

It was observed that when hexane was used as the organic solvent, a drop in the residual concentration of hexane was obtained from more than 10,000 ppm in the waste stream to no more than 120 ppm hexane in the waste water stream. By repeating said step e), the residual concentration of hexane in the waste water stream was further reduced to below 10 ppm. The invention also relates to a process for removing organic solvents, preferably hexane, from water, wherein a stream containing water and said solvent is mixed with steam to heat said stream up and to pressurize it; and subsequently flash-evaporating the organic solvent to obtain a waste water stream essentially free of solvent; and optionally repeating the process until a desired residual amount of said solvent in water is obtained. By essentially free of solvent is herein meant residual solvent amounts of less than 150 ppm, more preferably less than 100 ppm, even more preferably less than 50 ppm, most preferably less than 10 ppm. Preferably, said process for removing organic solvent from water operates within the parameters and conditions as presented hereinabove.

The lecithin or the gum recovered from the process of the present invention is purified, and substantially free of contaminants. In particular, the purified lecithin is substantially free of PAHs. With substantially free, it is meant that the lecithin contains less than about 10 µg/kg wet weight of PAH4. With PAH4, it is meant the combination of the following chemicals: benzo(a)pyrene, benzo(a)anthracene, benzo(b)fluoranthene and chrysene.

With the process of the present invention, it is further possible to obtain purified lecithin or purified gum having a PAH4 content of less than about 1.0 µg/kg wet weight, preferably even less than about 0.5 µg/kg wet weight, more preferably even less than about 0.3 µg/kg wet weight. The level of benzo(a)pyrene in the purified lecithin is preferably less than about 2 µg/kg wet weight, more preferably less than about 1 µg/kg wet weight, and even more preferably less than about 0.05 µg/kg wet weight.

The purified lecithin or purified gum is also substantially free of particulates.

The process of the present invention is also capable of removing contaminants beyond PAHs. As such, the purified lecithin or the purified gum is preferably also substantially free of pesticides, herbicides, insecticides, heavy metals and particulates.

The recovered purified lecithin or purified gum is preferably also substantially free of organic solvent. With substantially free of organic solvent, it is meant that the level of organic solvent in the lecithin or gum is less than about 5000 ppm, preferably less than about 3000 ppm, if ethanol is used as solvent, and less than about 10 ppm, preferably less than about 1 ppm, if hexane is used.

Preferably the resulting lecithin or gum shows a turbidity (1 wt % lecithin in hexane) of less than about 100 nephelometric turbidity units (NTU). In a highly preferred embodiment, the recovered lecithin is transparent which means that 1 wt % lecithin in hexane shows a turbidity of less than about 10 NTU. The NTU value of lecithin can be measured for example with a Hach® Ratio Turbidimeter 18900 or 2100. 1 g (+/−0.01) of lecithin is added to a glass beaker, and hexane is added up to 100 ml. Then mix the solution well. A measuring tube is filled with the mixture and inserted into the turbidity meter. The result, expressed in NTU, can be read from the device.

The invention also relates to a lecithin having an amount of hexane insoluble (HI) in solution, measured at a concentration of 40% lecithin in hexane, of at most 0.1%, more preferably at most 0.01%, most preferably at most 0.008%. The invention also relates to a lecithin having an amount of HI in solution, measured at a concentration of 20% lecithin in hexane, of at most 0.1%, more preferably at most 0.01%, yet even more preferably at most 0.005%, most preferably at most 0.003%. To inventors' knowledge, a lecithin having such low amounts of HI at such high concentration of lecithin in hexane solutions were not achieved hitherto. To determine HI, a known sample weight is dissolved in hexane and filtered under reduced pressure through a coarse-porosity filtering frit (porosity C) that has been previously dried (e.g. above 100° C. for at least 1 h) and weighted.

In one embodiment, the present invention relates to food and feed products comprising the purified lecithin. In a highly preferred embodiment, the present invention relates to an infant food product comprising the purified lecithin.

EXAMPLES

Sunflower lecithin was heated up to 50° C. Active carbon was added to the lecithin under stirring. The mixture was stirred for 19 hours at 50° C. and then cooled down to ambient temperature.

To the obtained dispersion, hexane was added (lecithin: hexane 20:80). This mixture was stirred for 15 minutes at ambient temperature.

The mixture was centrifuged at 4500 rpm for 5 minutes (centrifuge SIGMA 3K15, rotor 11133).

The samples were dried and analysed for PAH content. The results are presented in Table 1.

The following active carbon was used:

HF: Norit SA 4 PAH HF #94011-7 (Cabot Norit Netherlands B.V.)

Ultra: Norit SA Ultra PAH #8024-0 (Cabot Norit Netherlands B.V.)

Granulate: Norit GAC 1240 #602282 (Cabot Norit Netherlands).

TABLE 1

| Sample | PAH (µg/kg) |
| --- | --- |
| Sunflower lecithin (control) | Benzo(a)pyren 7.6 PAH4 33.8 |
| Sunflower lecithin + 0.2% HF | Benzo(a)pyren <0.5 PAH4 0.78 |
| Sunflower lecithin + 0.5% HF | Benzo(a)pyren <0.5 PAH4 0.78 |
| Sunflower lecithin + 0.05% Ultra | Benzo(a)pyren <0.5 PAH4 2.6 |
| Sunflower lecithin + 0.1% Ultra | Benzo(a)pyren <0.5 PAH4 1.0 |
| Sunflower lecithin + 0.2% Ultra | Benzo(a)pyren <0.5<br>PAH4 --- (below detection limit) |
| Sunflower lecithin + 0.5% Ultra | Benzo(a)pyren <0.5<br>PAH4 --- (below detection limit) |
| Sunflower lecithin + 0.2% Granulate | Benzo(a)pyren <0.5<br>PAH4 --- (below detection limit) |

The amount of hexane insoluble (HI) in the lecithin samples produced in Examples was analyzed for dilutions of lecithin of 40 wt % and 20 wt % in hexane and for two feeding rates of the mixture to the centrifuge. The results are presented in Table 2.

TABLE 2

| Lecithin Concentration % | Feed rate (% of processing capacity) | HI % |
|---|---|---|
| 20 | 34 | 0.003 |
| 20 | 68 | 0.002 |
| 20 | 68 | 0.001 |
| 40 | 34 | 0.009 |
| 40 | 68 | 0.007 |

A significant decrease in PAH removal was observed, versus the control sunflower lecithin. For all samples, the active carbon was separated from the sunflower lecithin.

The invention claimed is:

1. A method for the purification of lecithin, the method comprising:
   (a) mixing lecithin with active carbon to form a dispersion;
   (b) mixing an organic solvent into the dispersion; and
   (c) separating the active carbon and contaminants from the lecithin to achieve a purified lecithin;
   wherein the purified lecithin contains less than 10 μg/kg wet weight of benzo(a)pyrene, benzo(a)anthracene, benzo(b)fluoranthene and chrysene.

2. The method of claim 1, wherein the purified lecithin contains ethanol at a level of less than 5000 ppm or contains hexane at a level of less than 10 ppm.

3. The method of claim 1, wherein the purified lecithin has a turbidity of less than 100 nephelometric turbidity units.

4. The method of claim 1, wherein the purified lecithin contains at most 0.1% hexane insoluble.

5. The method of claim 1 wherein, in step (a), lecithin is at a temperature of from 10° C. to 90° C.

6. The method of claim 1, wherein the active carbon is mixed with the lecithin for a period of from 1 hour to 120 hours.

7. The method of claim 1, wherein the active carbon is powder active carbon.

8. The method of claim 1, wherein the active carbon is mixed with lecithin at a level of from 0.01% to 3% by weight of the lecithin.

9. The method of claim 1, wherein the organic solvent is mixed into the dispersion at a ratio of lecithin to organic solvent of from 3:1 to 1:20.

10. The method of claim 1, wherein the active carbon and contaminants are separated by means of a disk stack centrifuge or a decanter.

11. The method of claim 1, wherein the organic solvent is at a temperature of from 1° C. above its melting point to 1° C. below its boiling point.

12. The method of claim 1, wherein the organic solvent is separated from the lecithin.

13. The method of claim 1, further comprising the step of filtrating the lecithin.

14. A sunflower lecithin in liquid form showing a turbidity of less than 100 nephelometric turbidity units (NTU) when measured at 1 wt % lecithin in hexane, said lecithin having an amount of hexane insoluble (HI) in solution of at most 0.005% when measured at a concentration of 20% lecithin in hexane and having a poly-aromatic hydrocarbons (PAH4) content of less than 10 μg/kg wet weight of PAH4, wherein PAH4 is a combination of benzo(a)pyrene, 5 benzo(a)anthracene, benzo(b)fluoranthene and chrysene.

15. The lecithin of claim 14 comprising ethanol or hexane, wherein the ethanol level is less than 5000 ppm and the hexane level is less than 10 ppm.

16. A food or feed product comprising the lecithin of claim 14.

17. The food or feed product of claim 16, wherein the food product is an infant food product.

* * * * *